(12) United States Patent
Kirn et al.

(10) Patent No.: US 11,000,452 B2
(45) Date of Patent: May 11, 2021

(54) TEMPORARY TUBES AND A SYSTEM FOR PLACING SAME IN A PATIENT

(71) Applicant: Werd, LLC, Lexington, KY (US)

(72) Inventors: David S. Kirn, Lexington, KY (US); Richard D. Hisel, Nicholasville, KY (US); William Whitman, Lexington, KY (US)

(73) Assignee: WERD, LLC, Lexington, KY (US)

( * ) Notice: Subject to any disclaimer, the term of this patent is extended or adjusted under 35 U.S.C. 154(b) by 0 days.

(21) Appl. No.: 15/696,639

(22) Filed: Sep. 6, 2017

(65) Prior Publication Data
US 2017/0360288 A1 Dec. 21, 2017

Related U.S. Application Data

(63) Continuation of application No. PCT/US2016/041153, filed on Jul. 6, 2016.
(Continued)

(51) Int. Cl.
*A61B 1/06* (2006.01)
*A61B 1/07* (2006.01)
(Continued)

(52) U.S. Cl.
CPC ............ *A61J 15/0026* (2013.01); *A61B 1/05* (2013.01); *A61B 1/0676* (2013.01); *A61B 1/0684* (2013.01); *A61B 1/07* (2013.01); *A61B 1/126* (2013.01); *A61J 15/0003* (2013.01); *A61J 15/0096* (2013.01); *A61M 16/0418* (2014.02); *A61M 16/0427* (2014.02); *A61M 16/0488* (2013.01); *A61B 1/00124* (2013.01); *A61B 1/273* (2013.01); *A61M 3/0279* (2013.01);
(Continued)

(58) Field of Classification Search
CPC .. A61B 1/126; A61B 1/07; A61B 1/05; A61B 1/0676; A61B 1/0684; A61B 1/00089; A61B 1/00091; A61B 1/00101
USPC ........ 600/106–107, 139–142, 146–153, 156, 600/127, 129
See application file for complete search history.

(56) References Cited

U.S. PATENT DOCUMENTS

| | | | |
|---|---|---|---|
| 4,704,111 A | | 11/1987 | Moss |
| 5,621,830 A | * | 4/1997 | Lucey ................ A61B 1/00179 385/118 |

(Continued)

OTHER PUBLICATIONS

International Search Report of PCT/US2016/41153 dated Oct. 7, 2016.
(Continued)

*Primary Examiner* — Matthew J Kasztejna
(74) *Attorney, Agent, or Firm* — Michael S. Hargis; King & Schickli, PLLC (57) ABSTRACT

A temporary tube placement system includes a tube having a proximal end and a distal end, a camera supported by the tube at the distal end, a plurality of fiber optic filaments through which light from a light source travels from the proximal end to the distal end, a screen for displaying images from the camera, and a power source electrically attached to the camera and the light source. The enteral tube includes a tube having a distal end portion for placement within a patient and a proximal end portion and a lumen increasing in cross section from the proximal end portion toward the distal end portion along at least a portion of the tube.

19 Claims, 10 Drawing Sheets

Related U.S. Application Data (60) Provisional application No. 62/189,021, filed on Jul. 6, 2015.

(51) Int. Cl.
| | |
|---|---|
| *A61B 1/12* | (2006.01) |
| *A61B 1/273* | (2006.01) |
| *A61J 15/00* | (2006.01) |
| *A61M 16/04* | (2006.01) |
| *A61B 1/05* | (2006.01) |
| *A61B 1/00* | (2006.01) |
| *A61M 3/02* | (2006.01) |

(52) U.S. Cl.
CPC ..... *A61M 16/0463* (2013.01); *A61M 16/0465* (2013.01); *A61M 2205/3569* (2013.01); *A61M 2205/3584* (2013.01); *A61M 2205/3592* (2013.01); *A61M 2205/502* (2013.01)

(56) References Cited

U.S. PATENT DOCUMENTS

| | | | |
|---|---|---|---|
| 5,665,064 A | | 9/1997 | Bodicky et al. |
| 5,718,061 A | * | 2/1998 | Scheufler ............... B01D 46/00 34/475 |
| 5,913,816 A | * | 6/1999 | Sanders ................ A61B 1/267 600/114 |
| 6,582,395 B1 | | 6/2003 | Burkett et al. |
| 6,652,491 B1 | | 11/2003 | Walker et al. |
| 8,142,394 B1 | | 3/2012 | Rotella et al. |
| 8,361,041 B2 | * | 1/2013 | Fang ...................... A61B 1/042 604/264 |
| 2006/0111612 A1 | * | 5/2006 | Matsumoto ........ A61B 1/00089 600/129 |
| 2009/0318798 A1 | * | 12/2009 | Singh .................... A61B 1/012 600/424 |
| 2011/0046446 A1 | * | 2/2011 | Hirayama .......... A61B 1/00091 600/158 |
| 2012/0089128 A1 | | 4/2012 | Rotella et al. |
| 2012/0226104 A1 | * | 9/2012 | Ikeda ................. A61B 1/00091 600/129 |
| 2012/0316395 A1 | * | 12/2012 | Koga ................. A61B 1/00091 600/157 |
| 2013/0030249 A1 | | 1/2013 | Vazales et al. |
| 2013/0150667 A1 | * | 6/2013 | Mitamura .......... A61B 1/00089 600/104 |
| 2013/0172677 A1 | * | 7/2013 | Kennedy, II ........... A61B 1/051 600/112 |
| 2013/0231533 A1 | | 9/2013 | Papademetriou et al. |
| 2014/0039253 A1 | | 2/2014 | Fang et al. |
| 2014/0073853 A1 | | 3/2014 | Swisher et al. |
| 2014/0350335 A1 | | 11/2014 | Kezirian et al. |

OTHER PUBLICATIONS

Fisher, et al. "Clogged Feeding Tubes: A Clinicians Thorn" Nutrition Issues in Gastroenterology, Practical Gastroenterology, Series #127, Mar. 2014.

Hofstetter, et al. "Causes of non-medication-induced nasogastric tube occlusion" Nasogastric tub occlusion Reports, American Society of Hospital Pharmacists, AJHP vol. 49, Mar. 1992.

* cited by examiner

TEMPORARY TUBES AND A SYSTEM FOR PLACING SAME IN A PATIENT

This application is a continuation of international patent application number PCT/US16/41153 filed on Jul. 6, 2016, which in turn claims priority from U.S. Provisional Patent Application No. 62/189,021, filed Jul. 6, 2015, the disclosure of which is incorporated herein by reference.

FIELD OF THE INVENTION

This document relates generally to temporary tube placement, and more specifically with tapered temporary tubes and related systems and methods of placement in a patient.

BACKGROUND OF THE INVENTION

In the course of healthcare, temporary tubes such as enteral and endotracheal tubes are placed into the gastrointestinal tract or the respiratory tract, respectively, of patients for the delivery of nutrition or suction of the gastrointestinal tract and air to the respiratory tract.

Most commonly, these tubes are placed via the nose or mouth without guidance and therefore tube position must be confirmed radiographically after placement. While this method is simple and generally effective, the consequences of a misplaced tube can be significant. If food or liquid are delivered into the respiratory tract or if oxygen is delivered into the gastrointestinal tract rather than the respiratory tract, for example, the consequences can be fatal.

Although several methods of tube guidance have been developed, each has certain limitations. X-ray fluoroscopy, for example, is the dominant method for guided tube placement. Fluoroscopic guidance tracks the tube progress via its x-ray shadow. With knowledge of radiographic anatomy, the user can confirm that the tube has followed the correct path to a desired location. While effective, this method requires x-ray exposure to the patient and clinician, and requires additional equipment and a practitioner trained in the process all of which results in a significant cost. Even more, bedside placement of a tube is usually not possible with this method due to the size of the fluoroscopic equipment.

Another method of tube placement involves positional tracking on a system utilizing a simulated display. As described in US Published Patent Application No. 2013/0218006, the system monitors a position of a tip of the tube and provides a graphic representation of a path of the tip on a display. In other words, the system provides a graphic representation of the path of the tip, thereby allowing a skilled user to monitor the progress of the tip during placement. While this method may be utilized at the patient's bedside, it does not provide a confirmation with respect to the individual patient's anatomy and would not indicate if the tube had perforated through the wall of the gastrointestinal tract. The limitations of these methods underscore the need for a method which provides direct visualization for tube placement.

Along these lines, numerous visualization systems for endotracheal tube placement have been developed. A majority of these systems place a video camera or other visualization means on a laryngoscope. The laryngoscope provides retraction of the tongue and glottis thereby establishing and visualizing a pathway to the vocal cords, through which the endotracheal tube must pass to enter the trachea. Other of these systems utilize a video camera positioned within an end of the enteral tube. These systems utilize battery powered light emitting diodes (LEDs) positioned near the camera within the tip of the tube for illuminating the pathway of the tube.

Despite the advancement of a more direct method of visualization for the clinician, current video camera systems suffer from certain limitations associated with utilization of the camera. Specifically, the camera lens can become cloudy or obstructed by fluids and/or food debris during utilization thereby hindering the clinician's ability to visualize the pathway. Even more, the amount of light generated by the LEDs is insufficient to accommodate visualization primarily due to size and heat generation limitations. Accordingly, a need exists for a temporary tube placement system which provides a direct method of visualization. The system should provide a sufficient amount of light within the pathway without excessive heat and a means of cleaning fluid and/or food debris from the camera lens, as required, to ensure proper visualization for the clinician during placement of the tube.

Even enteral tubes properly placed by any of the above-described methods, however, suffer from drawbacks associated with their tendency to clog. Frequently, medications in pill form must be crushed and delivered down the enteral tube placed in the stomach or small bowel. These pill fragments have a tendency to clog tubes. Tube feeding solution is similarly prone to congealing and creating clogs. If clogs occur and are unable to be cleared, the tube must be withdrawn from the patient and replaced at added expense, and discomfort and risk to the patient. Accordingly, any tube placement system should further minimize the potential for clogging and also allow for easier clog removal in the event a clog occurs.

SUMMARY OF THE INVENTION

In accordance with the purposes and benefits described herein, a temporary tube, systems for placement of temporary tubes, and related methods are of tube placement are provided. The temporary tube may be broadly described as including a tube having a distal end portion for placement within a patient and a proximal end portion. The tube has a lumen increasing in cross section from the proximal end portion toward the distal end portion along at least a portion of the tube.

In one possible embodiment, the cross section is an inner diameter of the tube. In another, the tube includes at least one vent positioned in the distal end portion.

In another possible embodiment, the tube includes a tip attached to the distal end portion of the tube and the tip includes at least one vent. In yet another, the tip includes at least one wall adjacent a distal end of the tip for deflecting matter discharged from the at least one vent.

In still another possible embodiment, the lumen cross section is a maximum size at a distal end of the distal end portion. In another possible embodiment, the tube has an outer cross section increasing in size between the proximal end portion and the distal end portion. In yet another, the lumen cross section is a maximum size at the at least one vent. In yet another possible embodiment, the lumen cross section increases in size from the proximal end portion to the distal end portion of the tube.

In one other possible embodiment, the tube further includes a stylet for steering the tube during insertion. In another, the stylet is a nitinol wire for bending the distal end portion of the tube when a voltage is applied to the nitinol wire.

In one other possible embodiment, a temporary tube for placement within a patient includes a tube having a distal end portion and a proximal end portion, the tube having a lumen extending a length of the tube, a camera having an aperture and a lens, the camera positioned adjacent the distal end portion of the tube for positioning the tube during placement in the patient; and a light source providing light at a distal end of the tube.

In another possible embodiment, the tube lumen increases in cross section from the proximal end portion toward the distal end portion along at least a portion of the tube. In still another, the lumen cross section is a maximum size at the distal end. In yet another, the lumen cross section increases in size from the proximal end portion to the distal end of the tube.

In yet still another possible embodiment, the light source includes at least one light emitting diode. In another possible embodiment, the at least one light emitting diode is supported adjacent the camera.

In another possible embodiment, the system for placing a temporary tube in a patient further includes at least one fiber optic element extending along the tube, the at least one fiber optic element positioned adjacent the at least one light emitting diode at the proximal end of the tube and adjacent the tip at the distal end of the tube for guiding light from the at least one light emitting diode.

In still another possible embodiment, the tip includes at least one channel for directing a fluid onto the lens of the camera. In another, the system further includes an enclosure attached to the tube. In yet another, the enclosure includes a slide for retracting the at least one fiber optic filament and the camera from the tube. In one other possible embodiment, the enclosure includes a fitting for receiving irrigation fluid and in another the enclosure includes a video output cable.

In one other possible embodiment, the tip includes at least one channel for directing a fluid onto the lens. In another, the tube includes at least one vent positioned in the distal end portion of the tube and the at least one fiber optic filament occludes the at least one vent directing the fluid through the at least one channel.

In still another possible embodiment, the tip further includes at least one slot through which light guided through the at least one fiber optic element exits.

In one other possible embodiment, a temporary tube includes a tube having a proximal end and a distal end, a stylet for steering the tube during insertion, a camera having an aperture and a lens, the camera attached to the stylet, and a light source positioned adjacent the distal end of the tube.

In still another possible embodiment, the tube further includes a stylet for steering the tube during insertion. In another, the enteral tube further includes a power source, and the stylet is a nitinol wire for bending the distal end portion of the tube when a voltage from the power source is applied to the nitinol wire.

In still one other possible embodiment, a temporary tube placement system includes a tube having a proximal end and a distal end, a camera supported by the tube at the distal end, a plurality of fiber optic filaments through which light from a light source travels from the proximal end to the distal end, a screen for displaying images from the camera, and a power source electrically attached to the camera and the light source.

In another possible embodiment, the screen is a smart phone screen. In still another possible embodiment, the enteral tube placement system further includes a recording device for recording the images from the camera.

In accordance with another aspect, a method of placing a temporary tube in a patient is provided. The method may be broadly described as comprising the steps of: (a) inserting an end of a tube having a lumen increasing in cross section from a proximal end portion toward a distal end portion along at least a portion of the tube into the patient; (b) positioning a camera and a plurality of fiber optic filaments within a lumen of the tube; (c) monitoring a display to determine a position of the end of the tube; and (d) guiding the end of the tube utilizing a stylet until a desired position for the end of the tube is achieved.

In one other possible embodiment, the method further includes the step of placing an irrigation fluid into the tube when a lens of the camera becomes obscured by mucous or other material in the gastrointestinal tract. In still another, the method further includes the steps of withdrawing the plurality of fiber optic filaments and the stylet to a position proximal to the camera, and removing the plurality of fiber optic filaments, the stylet, and the camera from a proximal end of the tube.

In the following description, there are shown and described several preferred embodiments of temporary tubes and systems for placing same. As it should be realized, the tubes and placement systems are capable of other, different embodiments and their several details are capable of modification in various, obvious aspects all without departing from the tubes and systems as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the invention and method and together with the description serve to explain certain principles thereof. In the drawing figures.

Reference will now be made in detail to the present described embodiments of the invention and related method, examples of which are illustrated in the accompanying drawing figures, wherein like numerals are used to represent like elements.

DETAILED DESCRIPTION

Figure 1:
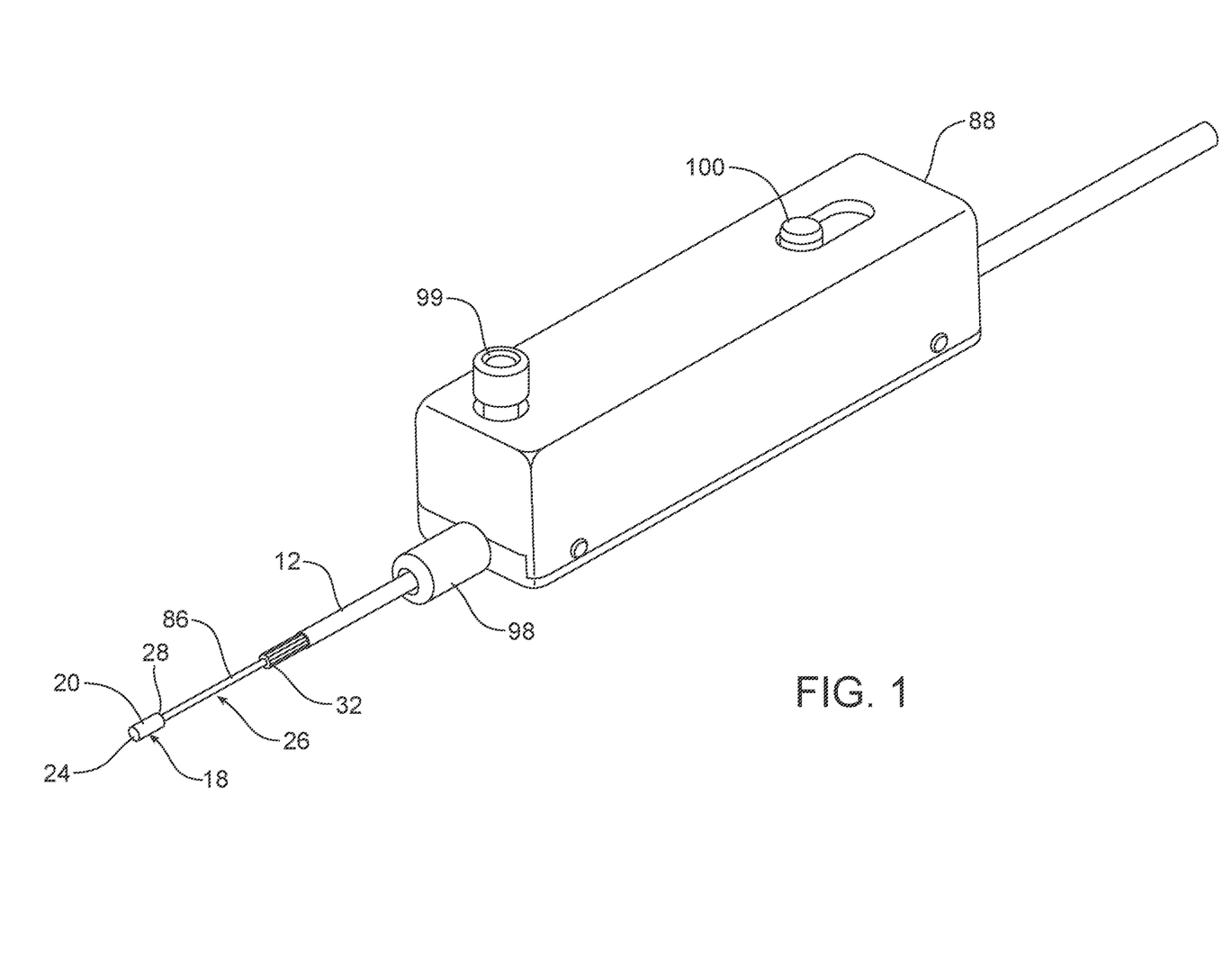
FIG. 1 is a perspective view of a tube placement system including a control enclosure.

Reference is now made to FIG. 1 which partially illustrates a system 10 for placing an enteral tube in a patient (P). Enteral tubes include, but are not limited to, nasogastric tubes, nasoduodenal tubes, oral gastric tubes, oral duodenal tube, and feeding tubes located distal to the duodenum. Alternatively, the system 10 may be utilized to place endotracheal tubes which are designed to reside in the patient's trachea and enter the body through the mouth or the nose.

In the described embodiment, the system 10 includes a tube 12 having a proximal end portion 14 and a distal end portion 16 for placement within the patient. A video camera 18 positioned within a housing 20 is located at the distal end portion 16 of tube 12. The camera 18 includes an aperture 22 covered by a lens 24, as is known in the art, and a cable 26 is connected to the camera 18 and extends through a rear wall 28 of the housing 20. In an alternate embodiment, the cable 26 may include a connector at its distal end for connection to a mating connector mounted on the rear wall 28 of the camera housing 20. Either way, the cable 26 extends along the tube 12 providing a signal external to the patient (P) and power to the camera 18 as will be described in more detail below.

In the described embodiment, the camera 18 is positioned in a lumen 30 of the tube 12 and is removable after placement within the patient (P). The camera 18 may be a single use disposable camera or a multiple use camera suitable for cleaning and/or sterilization. Alternatively, the camera 18 may be contained in a disposable sheath (not shown) having an optically clear end positioned adjacent the camera lens 24. After placement of the tube 12 and removal of the camera 18, the sheath would be discarded and a new sheath utilized in a subsequent use of the camera 18.

As further shown in FIG. 1, a plurality of fiber optic filaments 32 extend within the lumen 30 generally adjacent an interior wall of the tube 12 and guide light from an external light source onto an area of the gastrointestinal or GI tract adjacent the camera 18. In the described embodiment, the external light source is a plurality of high intensity light emitting diodes or LEDs which may be positioned adjacent ends of the fiber optic filaments 32 utilizing heat shrink sleeves or otherwise as is known in the art.

Figure 2:
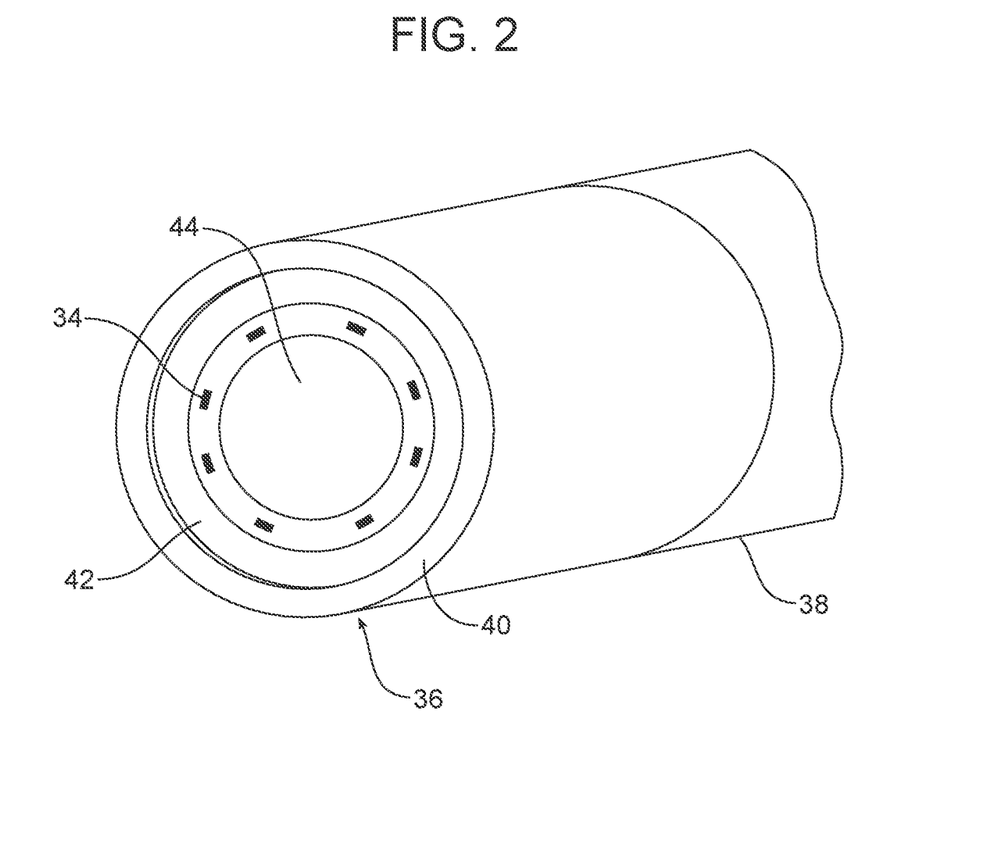
FIG. 2 is an enlarged perspective view of a distal end portion of the tube and camera.

Of course, other light sources may be utilized in alternate embodiments as shown in FIG. 2, for example. In this embodiment, miniature LEDs 34 are positioned near a camera 36 to provide illumination of the patient's GI tract during insertion of a tube 38. The camera 36 is contained within a watertight housing 40 and a lens 42 covers camera aperture 44 as well as the LEDs 34. While suitable in most instances, the intensity of the illumination provided in this alternate embodiment may be improved upon.

One way to increase the intensity of the illumination is to utilize larger, high intensity LEDs 46. In the described embodiment wherein fiber optic filaments 32 are utilized to guide light from the LEDs 46 positioned outside of the patient and into the patient's GI tract, the larger LEDs (e.g., high intensity LEDs) may be utilized. This is due to a lack of size limitation created by placement within the tube 12 and less concern with heat generated thereby because the LEDs 46 are positioned outside of the patient (P).

Figure 3:
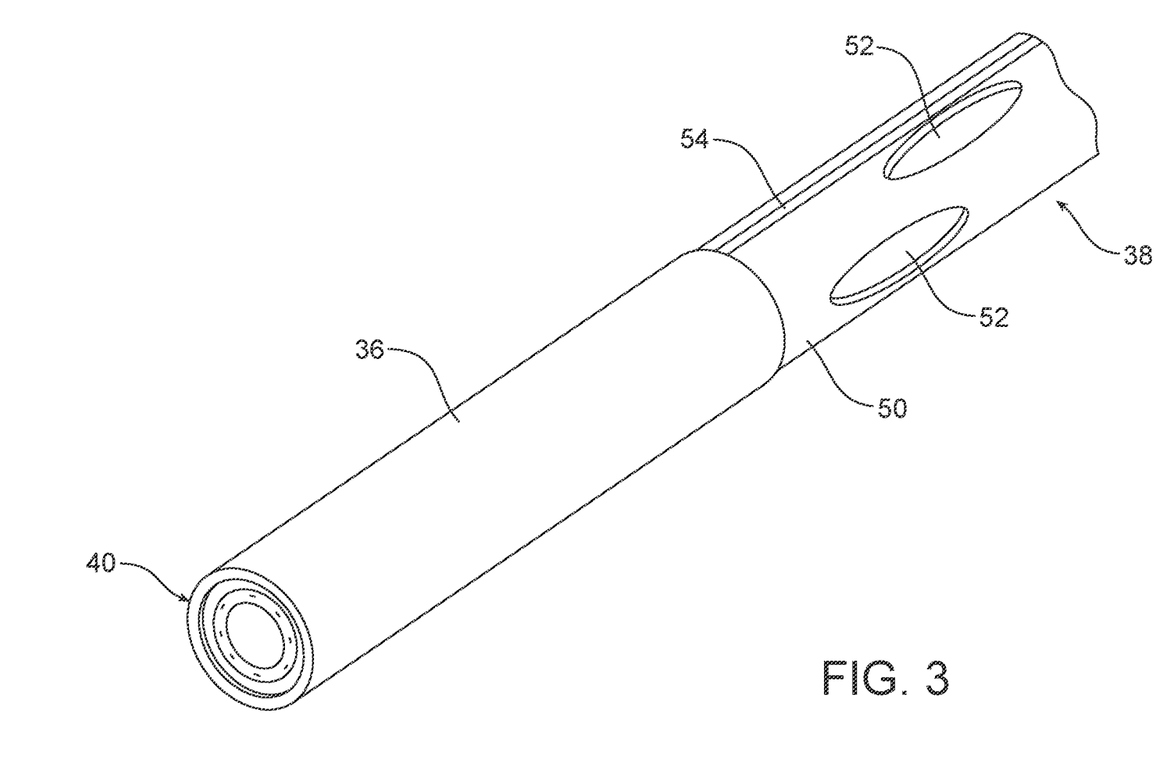
FIG. 3 is an enlarged perspective view of the distal end portion showing the camera and an alternate LED light source configuration.

As shown in FIG. 3, the camera 36 utilized in the alternate embodiment is located at a distal end portion 48 and is preferably contained within or contiguous with an outer cross section of the tube 38. In this embodiment, the camera 36 remains with the tube 38 for its duration of use. The camera 36 and LEDs 34 may be integrally molded and contained within an outer wall of the tube providing a smooth surface along the entire exterior of the tube. A multiplicity of vents 52 are located within the tube 38 along its distal end portion 48, but proximal to the camera 36 to discharge matter into the patient.

In the alternate embodiment, the tube wall 50 consists of a double layer of flexible material having a wire harness 54 positioned between the layers and apart from the working lumen used for the therapeutic purpose of the tube 38 such as feeding or suction. In other alternate embodiments, the tube wall 50 may be a single layer with a separate channel for harness 54 to keep it isolated from the liquid materials passing through the working lumen of the tube 38.

Figure 4:
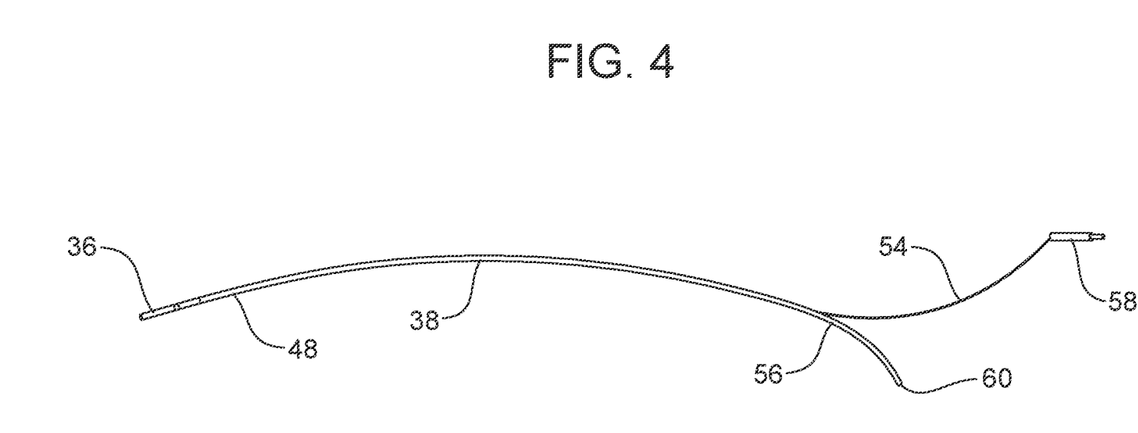
FIG. 4 is a perspective view of an alternate tube placement system wherein the camera and light source are fixed at a distal end portion of the tube.

As shown in FIG. 4, industry standard connectors (not shown) may be located at a proximal end portion 56 of the tube 38. An electrical connector 58 may be located separate from the tube 38 or attached at the proximal end portion 56 adjacent proximal end 60. The wiring harness 54 runs from the camera 36 and LEDs 34 to the proximal end portion 56 of the tube 38 where the connector 58 is located. A power supply and signal processing electronics for operation of the camera 36 and LEDs 34 may be located external to the tube 38 and are attached on a temporary basis as needed, such as during insertion. In addition, a flexible, steerable stylet 62 may be used via placement within the lumen of the tube 38 at the proximal end 60, and is also not shown in this figure.

In the embodiment shown in FIG. 1, the camera cable 26 and a stylet 86 extend centrally within the plurality of fiber optic filaments 32. The stylet 86 is provided to stiffen and guide the tube 12 during initial insertion. In the described embodiment, a nitinol wire (aka "a memory wire") is used to create a deflection at the distal end portion 16 of the tube 12. Using the video images provides by the camera 18, steering only requires a tip 74 of the tube 12 to bend in one direction since the tube can be rotated.

The nitinol material has the physical property of existing in one shape under normal circumstances, but will transform to a different configuration when an electrical voltage or current is applied thereto. For this application, the nitinol stylet would have a straight configuration as its norm or baseline. If the clinician desires the distal end portion 16 of the tube 12 to turn, an electrical current/voltage from a power supply 90 is applied to the nitinol wire and an end of the nitinol wire will take on its alternate or memory configuration of a bend. To do so, the clinician activates a switch or potentiometer (not shown) to send a current/voltage to the nitinol stylet 86 creating the variable deflection of the distal end portion 16.

In one alternate embodiment, two nitinol wires may be utilized with memory bends in differing directions to provide alternative steering options. In another alternate embodiment, the fiber optic filaments 32 may be used to generate deflection of the distal end portion 16 of the tube 12 for steering.

In addition to the nitinol stylet 86 described, steering of the tube 12 may alternatively be provided by a two component stylet in which one wire remains stationary and the other moves linearly against the first wire. The stationary and moving wires are rigidly attached only at their proximal ends. An outer sheath or a series of connectors binds the two components together while allowing linear slide of the moving component. Thus, a deflection is created at the proximal end portion 14 of the tube 12 as the moving wire is advanced or withdrawn relative to the stationary wire.

In another alternate embodiment, the camera 36 and LEDs 34 may be attached to a proximal end of the stylet 62 rather than the tube 38. Thus, the camera 36 and LEDs 34 can be withdrawn through the lumen of the tube or external to the lumen after placement. In this alternate embodiment, a cable for video signals as well as power would run parallel or within the stylet 62. The cable and stylet 62 may further be contained within a sheath which also includes or integrates with the camera 36. A connector may be located on a proximal end of the stylet.

Figure 5:
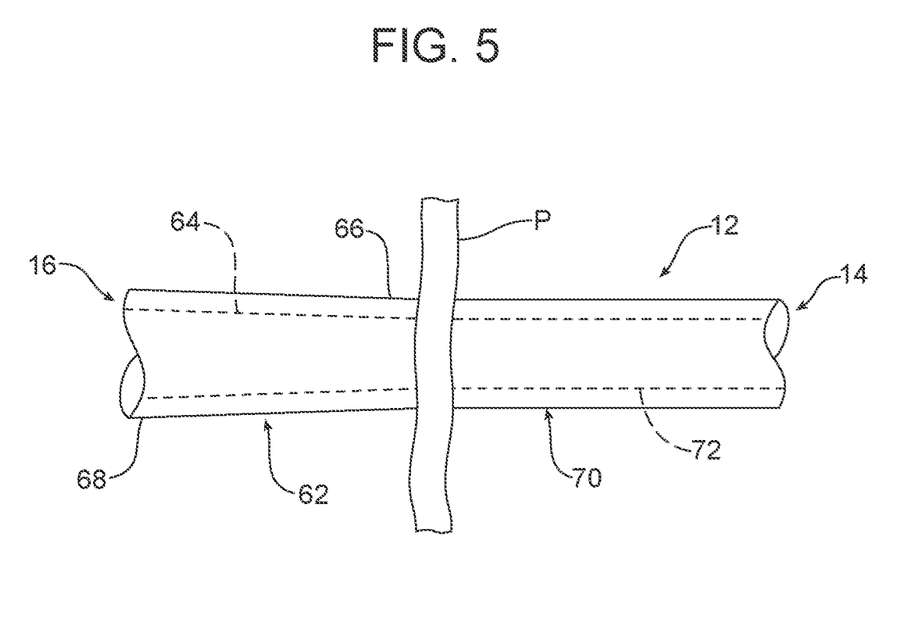
FIG. 5 is a partial plan view of a tube having a gradually increasing lumen cross section in a portion positioned within a patient.

As best shown in FIG. 5, the tube 12 in the initial described embodiment has a tapered configuration. In other words, a portion 62 of the tube 12 which will reside within the patient (P) will have a gradually increasing lumen cross section 64 from a proximal end 66 to a distal end 68. The portion 70 of the tube 12 which remains external to the patient (P) may have a uniform lumen cross section 72 or, in an alternate embodiment, the tapered lumen cross section may extend along the entirety of the tube 12 or along a portion thereof. For example, the lumen cross section may gradually increase from a proximal end portion of tube 12 toward a distal end or a distal end portion of the tube 12. Even more an outer cross section of the tube may be uniform or may gradually increase in areas where the lumen cross section gradually increases. If the tube 12 is round, the lumen cross section will necessarily be an inner diameter of the tube.

The purpose of providing a gradually increasing lumen cross section is to provide a smaller cross section at the area which would be best for patient comfort, such as the portion of the tube 12 residing in the nose. Then, distal to this, having the gradual increase in cross section makes clogging less likely. When the tube 12 is in place, the patient (P) will not be able to detect the larger cross section of the tube 12 distally.

Further, should a clog develop in the tapered portion 62 of the tube 12 within the patient (P), gentle pressure with a suitable fluid flush will make clearing the clog more likely than with a uniform lumen cross section. To further diminish the risk of clogging, an interior surface of the tube 12 may be coated in a non-stick or lubricious material. Clogs located in the constant lumen cross section portion 70 of the tube 12 would be mostly external to the patient (P). In this portion 70, external pressure may also be applied by the clinician to the tube 12 to milk or break up the clog and enhance clearing along with fluid flush.

Figure 6:
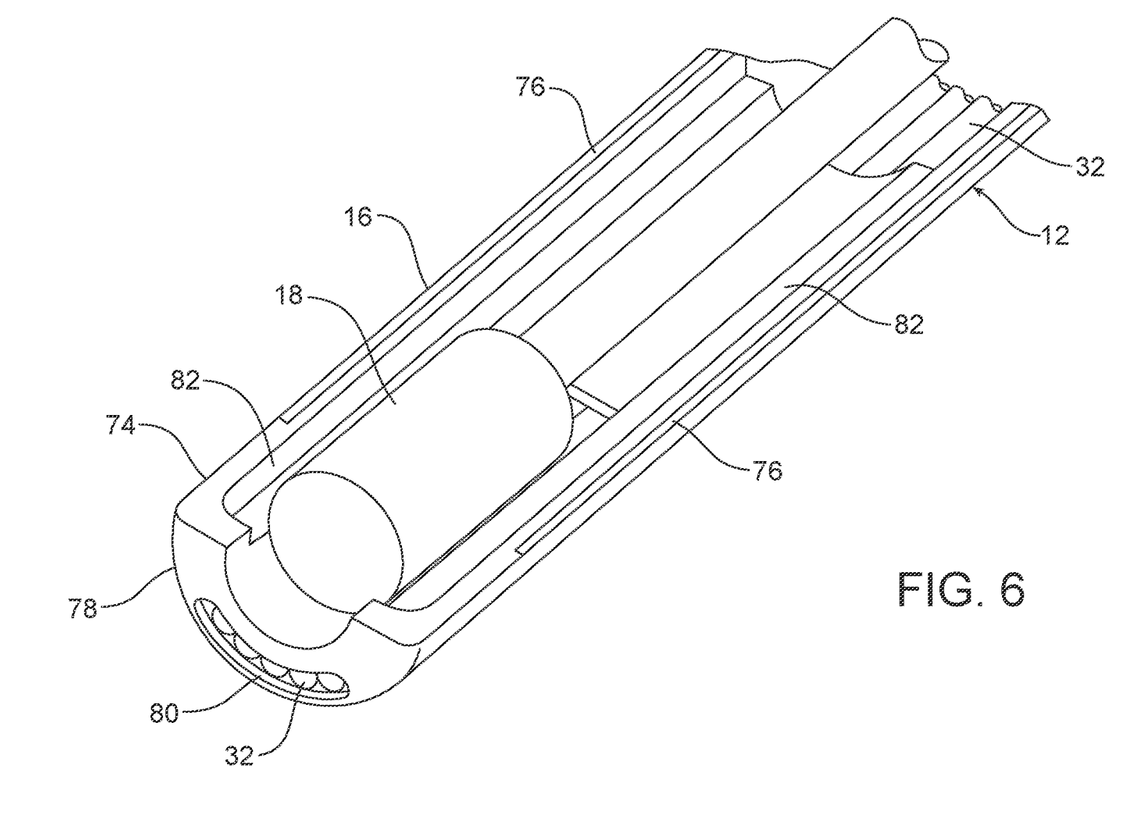
FIG. 6 is a cross section of a perspective view of a tip supported by the tube for supporting the camera and fiber optic filaments.

As shown in FIG. 6, the described system 10 for placing an enteral tube in a patient (P) further includes a tip 74 (shown in cross-section for clarity) supported at the distal end portion 16 of tube 12. The tip 74 includes a flange 76 received within the lumen 30 of the tube 12 for securing the tip within the tube. The camera 18 is positioned within the tip 74 and the camera cable 26 extends from the camera along the tube 12. In addition, the plurality of fiber optic filaments 32 extend within the tube 12 and terminate adjacent a distal end 78 of the tip 74. A slot or aperture 80 allows light guided through the fiber optic filaments 32 from the LEDs 46 to exit the tip 74 and illuminate the area around the tip within the patient (P).

As further shown, irrigation channels 82 are formed in the tip 74. If the camera lens 24 becomes obscured by mucous or other material in the gastrointestinal tract, a fluid is placed into the tube 12 and directed across the camera lens 24 via the irrigation channels 82. Further, if the development of an optical cavity is needed, air may be insufflated through the irrigation channels 82 using an irrigation fitting to enhance visualization.

Figure 7:
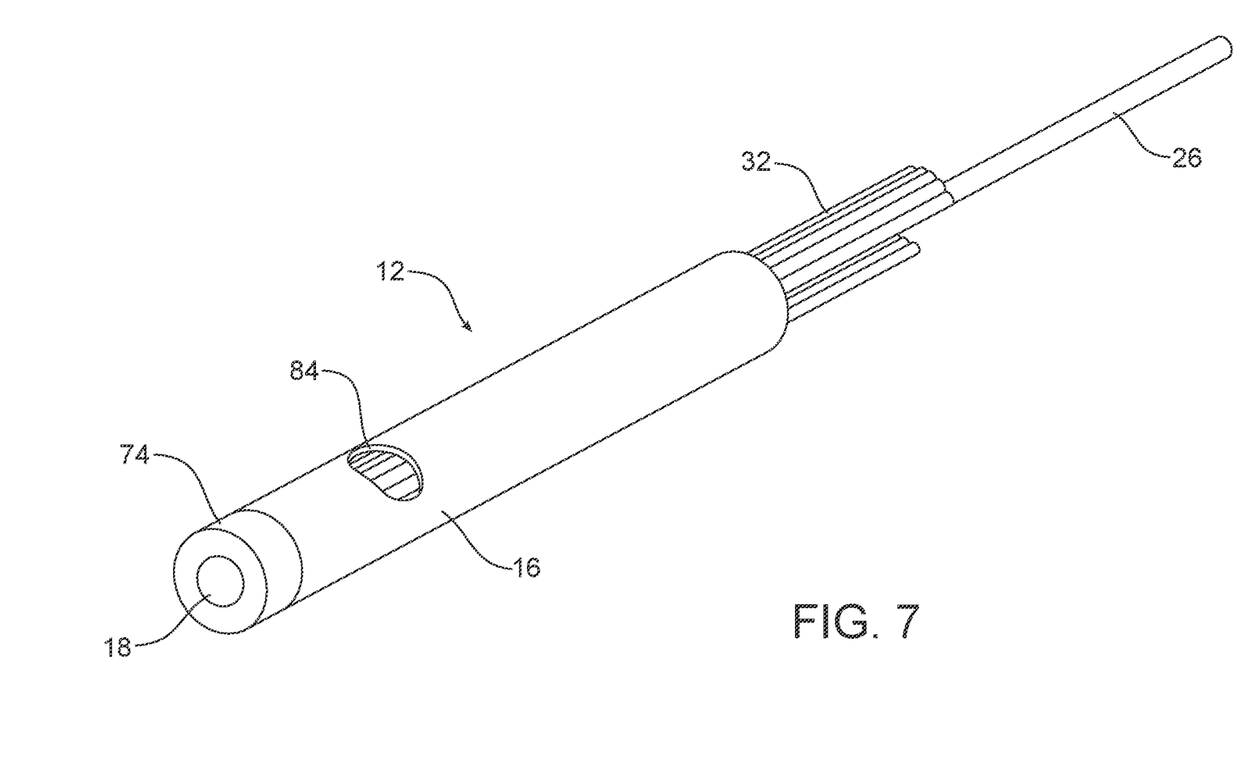
FIG. 7 is a perspective view of the tip supported by the tube showing the camera cable and fiber optic filaments extending beyond a portion of the tube.
Figure 8:
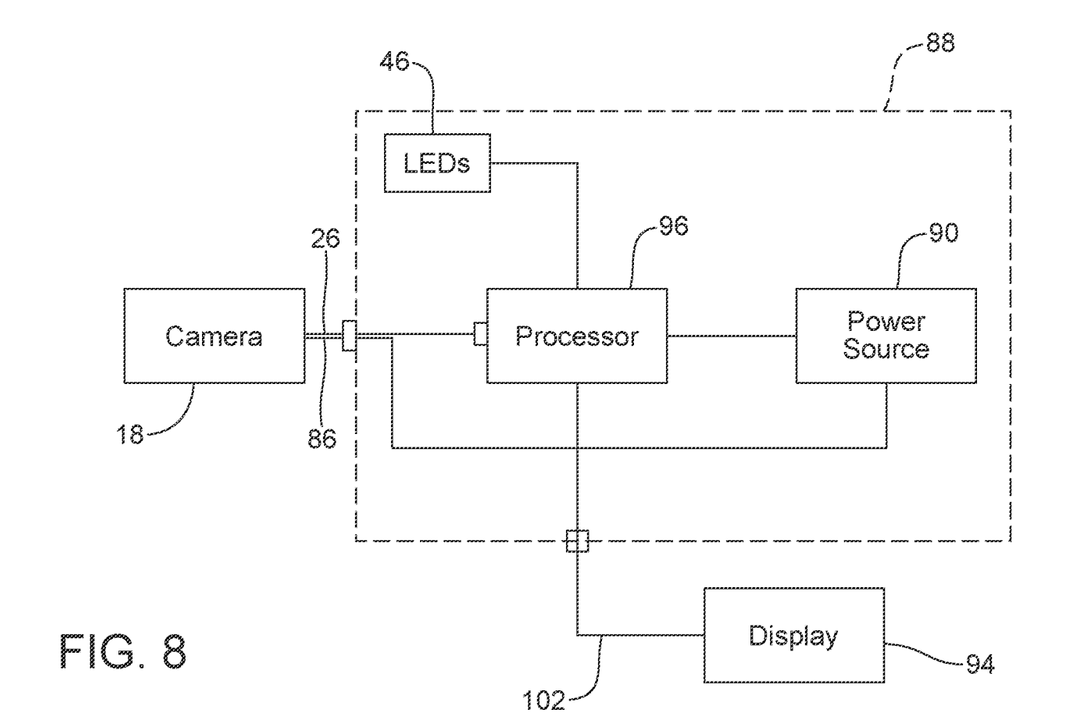
FIG. 8 is a schematic diagram of the tube placement system.

As shown in FIG. 7, a vent 84 is formed in the distal end portion 16 of the tube 12 to discharge matter into the patient (P). Although only one vent 84 is shown, a second vent is positioned opposite the vent 84 in the described embodiment and additional vents may be utilized in alternate embodiments if desired. As shown, the vent 84 is occluded by the fiber optic filaments 32 which is the norm during insertion of the tube 12. In this arrangement, the fiber optic filaments 32 prevent fluid placed into the tube to clean the camera lens 24 from escaping the tube into the patient prior to entering the irrigation channels 82 and onto the camera lens. In an alternate embodiment, a separate flap or portion of the camera or disposable camera sheath may serve to direct irrigation fluid flow across the lens, rather than the fiber optic filaments/irrigation channels.

When the tube 12 has been successfully navigated into position within the patient (P), the camera 18, fiber optic filaments 32, and stylet 86 are retracted from the tube leaving the tube and the tip 74 in place within the patient. This process is described in additional detail below, however, retraction of the fiber optic filaments 32 opens the vent 84 and allows for medicines, fluids, food, or the like to exit the tube 12 into the patient (P).

In the described embodiment of the system 10, the camera 18, fiber optic filaments 32, and a stylet 86 all terminate proximally in an enclosure 88. As shown schematically in FIG. 9, the enclosure 88 contains a power source 90, a video display 94, and a processor 96 for processing the signals from the camera. In an alternate embodiment, at least portions of the signal processing electronics (e.g., a processor) may be located adjacent to the camera 18 in the distal end portion 16 of the tube 12.

Figure 9:
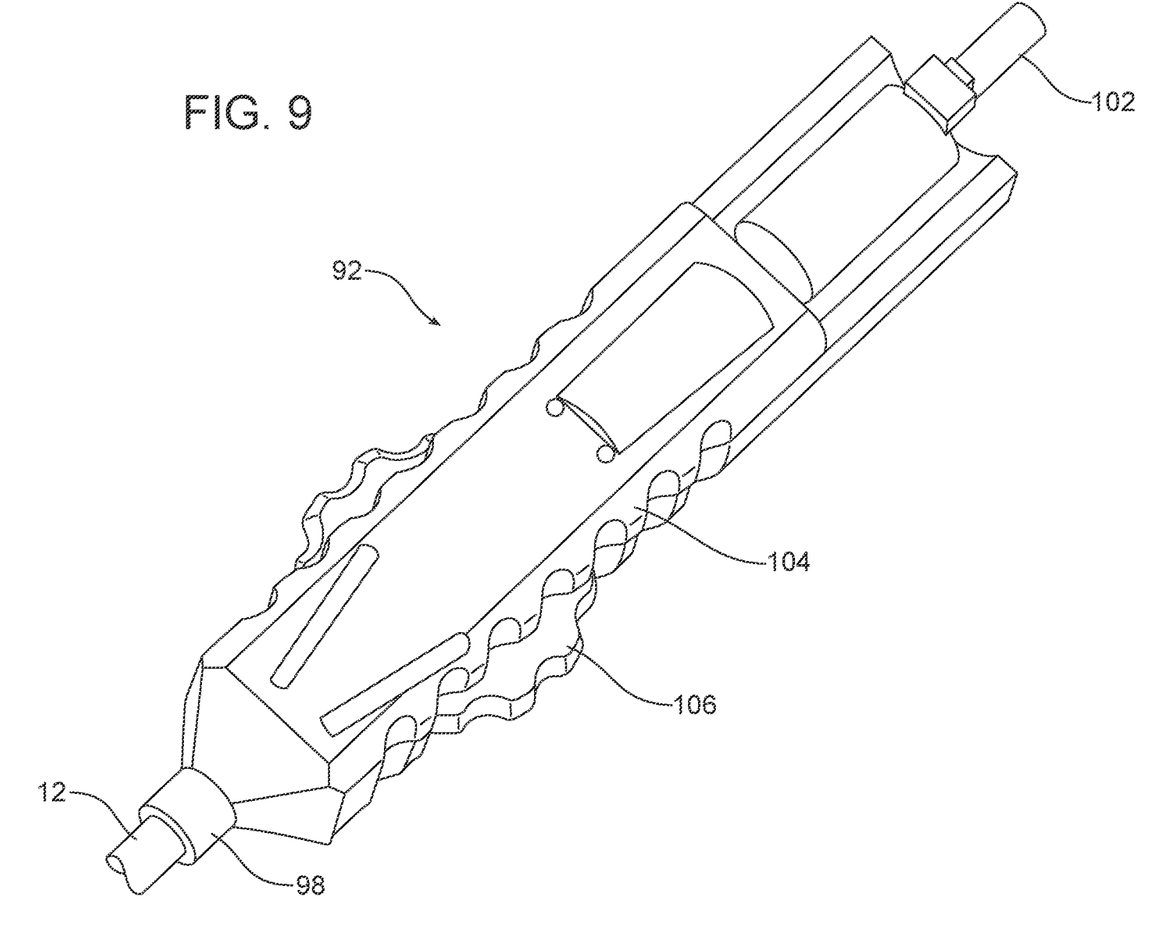
FIG. 9 is an alternate embodiment of an enclosure combining a steering mechanism for guiding the tube into the patient.

The enclosure 88 further includes a releasable fitting or collet 98 which grips the tube 12 ensuring that the camera 18, fiber optic filaments 32, and stylet 86 remain in position during placement. In addition, a fitting 99, for example a Luer lock fitting, is mounted to the enclosure 88 to attach a syringe or pump for irrigation of the tube.

Due to the tapered design of the tube 12, the proximal end portion 14 through which the camera 18, fiber optic filaments 32, and stylet 86 must pass has a smaller lumen cross section than the distal end portion 16. Thus, the sequenced or staged removal of the camera 18, fiber optic filaments 32, and stylet 86, as shown in FIG. 1, is required in order to allow the camera to pass through the proximal end portion 14 of the tube 12.

Accordingly, the stylet 86 and fiber optic filaments 32 must be removed before the camera 18 which has a larger diameter than the cable 26 to which it is attached. More specifically, the fiber optic filaments 32 and stylet 86 are withdrawn partially or completely first so that they may pass through the proximal end portion 14 of the tube 12 alongside of the camera cable 26 only. Then, the larger camera housing 20 which occupies nearly the entire lumen cross section of the tube 12 is withdrawn.

The staged removal of these components is accommodated by the enclosure 88. In the described embodiment, the clinician moves an enclosure mounted slide 100 which partially withdraws the fiber optic filaments 32 and stylet 86 so that their distal portions are now proximal to the camera 18. Simultaneously, the fitting 98 gripping the proximal end portion 14 of the tube 12 is released. The clinician holds the proximal end portion 14 of the tube 12 while the camera 18, fiber optic filaments 32, and stylet 86 are withdrawn from the tube by pulling the enclosure 88. The clinician then attaches an industry standard connector for feeding or suction systems, such as the ENFit connector, to the proximal end of the tube 12. In other embodiments wherein the lumen cross section is constant throughout the tube, withdrawal of the noted items may occur simultaneously.

In the described embodiment, the display 94 is attached to the enclosure 88 and processor 96 via a video output cable 102 for displaying images from the camera 18. In an alternate embodiment, the display or screen may be remotely positioned including, for example, on a handheld computing device, a smart phone, or other remote display that receives information from the processor via WIFI, Bluetooth, or other transmit and receive mechanisms. Even more, a recording device for recording the images from the camera may be used.

In an alternate embodiment shown in FIG. 9, a steering controller 92 may be utilized to guide the tube 12 into the patient (P) via the stylet 86 which is provided to stiffen and guide the tube 12 for initial insertion. As shown, an enclosure 104 combines the elements of the enclosure 88 with a thumb wheel 106 for changing direction of the distal end portion 16 of the tube 12 during insertion.

In operation, the clinician connects the tube 12 to the enclosure 88 which provides power to the camera 18 and LED's 46 illuminating the fiber optic filaments 32. The video data from the camera 18 is displayed on the display 94. A stylet 86 is positioned in the lumen cross section of the tube 12 to stiffen and guide the tube during insertion.

The clinician then inserts the distal end portion 16 of the tube 12 into the patient (P) via the nose or mouth. The camera 16, located within the distal end portion 16 of the tube 12, provides the clinician with a view of the path the tube is following as it is advanced. If the clinician identifies that the tube 12 is passing into the trachea instead of the esophagus, the clinician may withdraw the tube and re-advance. Further, steering is possible by means of the stylet 86.

The fiber optic filaments 32 provide illumination of the internal body cavities. Thus, this process is similar to endoscopy which is performed routinely for diagnostic and therapeutic purposes. The clinician continues to advance the tube 12 until the desired destination within the GI tract is reached. The interior portion of each segment of the GI tract has a characteristic appearance thus allowing positive identification of the tip 74 of the tube 12. Also, as with endoscopy, if the camera lens 24 becomes obscured by mucous or other material in the GI tract, irrigation is placed into the tube 12 via fitting 99 and directed across the camera lens by the irrigation channels 82.

When the desired position of the distal end portion 16 of the tube 12 has been achieved, the clinician activates the slide mechanism 100 which partially withdraws the fiber optic filaments 32 and stylet 86 so their distal portions are now proximal to the camera housing 20. Simultaneously, the fitting 98 which clamped the proximal end portion 14 of the tube 12 is released. The clinician holds the proximal end portion 14 of the tube 12 while the enclosure 88, camera 18, fiber optic filaments 32, and stylet 86 are withdrawn as described in detail above. The clinician then attaches an industry standard connector to the proximal end of the tube 12.

In the event a clog occludes flow of tube feeding materials, the clinician attaches a syringe (not shown) filled with water or other unclogging fluid to the fitting 99. Pressure generated by the syringe and fluid column will apply a forward force to the clog. This will push the clog distally to a portion of the tube 12 where the lumen cross section is slightly larger. When distal movement has been achieved, friction will decrease and the clog will pass forward from that point.

In the secondary embodiment where the system 10 is utilized for placement of an endotracheal tube, the camera 36 and LEDs 34 are positioned proximally on the end of a semi-rigid stylet which resides temporarily within the lumen of the tube 38. Video information is displayed on the display located at the distal aspect of the tube 38. First, the clinician inserts the camera 36 and semi-rigid stylet into the tube 38. In the preferred embodiment, the video display is attached to the proximal end of the endotracheal tube 38 leaving the clinician one hand for the laryngoscope and the other for the endotracheal tube with attached video system. Then, the clinician inserts the tube 38 into the patient's mouth or nose.

As noted, a laryngoscope may be utilized to provide retraction of the tongue and epiglottis thereby exposing the vocal cords. The vocal cords would be seen on the display 94 as the tube 38 is advanced toward and ultimately through them into the patient's trachea. With endotracheal intubation, precise placement is extremely important. If the tube 38 is not advanced far enough, injury to the vocal cords or inadvertent removal of the tube can result. If the tube 38 is advanced too far, it will usually proceed down the right mainstem bronchus. In this situation, the left side of the lung will not receive adequate ventilation leading to lung collapse, pneumonia, oxygen deficiency or other life threatening problems. When the tube 38 has been advanced to the proper position as confirmed by the video image, the stylet 86 with attached camera 36 and LEDs 34 are withdrawn leaving the tube 38 in place.

In summary, numerous benefits result from a system 10 for placing a temporary tube in a patient as illustrated in this document. The system 10 provides a temporary tube placement system with a direct method of visualization. In addition, the system 10 provides a sufficient amount of light within the pathway without excessive heat and provides for cleaning fluids and/or food debris from the camera lens to ensure proper visualization for the clinician during placement of the tube. Even more, the system minimizes the potential for clogging and allows for easier clog removal in the event a clog occurs by utilizing tubes having lumen cross section which gradually taper.

Figure 10:
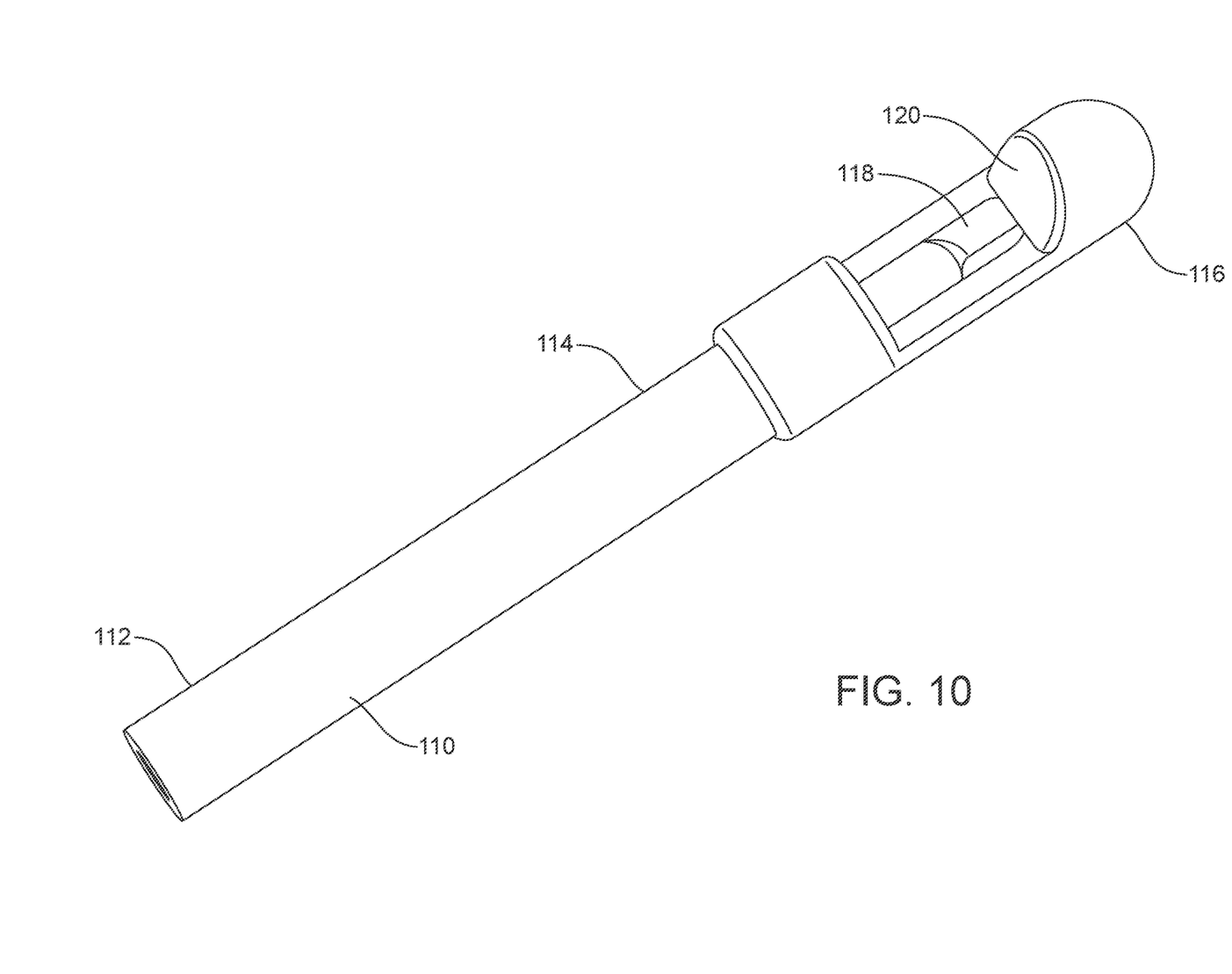
FIG. 10 is an alternate embodiment of a temporary tube having a tip attached at a distal end thereof.

The foregoing has been presented for purposes of illustration and description. It is not intended to be exhaustive or to limit the embodiments to the precise form disclosed. Obvious modifications and variations are possible in light of the above teachings. For example, temporary tube placement may be accomplished without video camera assistance as shown in FIG. 10. In this embodiment, the tube 110 has a lumen increasing in cross section from a proximal end portion 112 to a distal end portion 114 along at least a portion of the tube. A tip 116 is attached to a distal end of the tube 110 and includes a pair of vents 118. A wall 120 is positioned adjacent a distal end of each vent 118 for deflecting medicines, fluids, food, or the like from the vent into the patient (P). All such modifications and variations are within the scope of the appended claims when interpreted in accordance with the breadth to which they are fairly, legally and equitably entitled.

What is claimed:
1. A temporary tube placement system, comprising:
 a tube having a lumen extending between a proximal end and a distal end;
 a camera supported by said tube at said distal end;

a plurality of fiber optic filaments through which light from a light source travels from the proximal end to the distal end;

a screen for displaying images from said camera; and a power source electrically attached to said camera and said light source, wherein said tube includes at least one laterally-facing vent positioned in a distal end portion of said tube and located on an outer circumferential surface of the tube between the proximal end and the distal end of said tube and said plurality of fiber optic elements occludes said at least one laterally-facing vent when said plurality of fiber optic elements terminate at said distal end such that fluid is prevented from escaping the tube through said at least one laterally-facing vent.

2. The temporary tube placement system of claim 1, further comprising a tip for supporting said camera and said plurality of fiber optic filaments.

3. The temporary tube placement system of claim 2, wherein said tip includes an irrigation channel through which fluid from the proximal end of said tube passes to irrigate said lens.

4. The temporary tube placement system of claim 1, wherein a lumen of said tube increases in cross section from said proximal end toward said distal end along at least a portion of said tube.

5. The temporary tube placement system of claim 1, wherein the plurality of fiber optic filaments are configured to be retracted when the tube is positioned within the patient such that said at least one laterally-facing vent is open for fluid to exit the tube into the patient.

6. A temporary tube placement system, comprising:

a tube for placement within a patient having a distal end portion and a proximal end portion, the tube having a working lumen extending a length of the tube and at least one vent located on an outer circumferential surface of the distal end portion of the tube;

a camera positioned within and at least partially occluding the working lumen adjacent the distal end portion of the tube during placement in the patient;

a tip attached to the distal end portion of the tube, the tip having at least one channel for directing fluid onto a lens of the camera;

a light source providing light at a distal end of the tube; and a plurality of fiber optic filaments guiding light from the light source to the distal end of the tube during placement in the patient, wherein the camera is positioned inboard of the plurality of fiber optic filaments and the tip, and the plurality of fiber optic elements occlude the at least one vent such that fluid within the working lumen of the tube is prevented from escaping through the at least one vent.

7. The temporary tube placement system of claim 6, wherein the plurality of fiber optic filaments extend beyond an end of the tube into the tip.

8. The temporary tube placement system of claim 7, the tip includes a flange received within the working lumen of the tube for securing the tip to the tube.

9. The temporary tube placement system of claim 7, wherein the tip abuts the distal end of the tube.

10. The temporary tube placement system of claim 7, wherein the camera and the plurality of fiber optic filaments are independently retractable through the tube.

11. The temporary tube placement system of claim 7, wherein the working lumen of the tube increases in cross section from the proximal end portion toward the distal end portion along at least a portion of the tube.

12. The temporary tube placement system of claim 6, the tip includes a flange received within the working lumen of the tube for securing the tip to the tube.

13. The temporary tube placement system of claim 12, wherein the tip abuts the distal end of the tube.

14. The temporary tube placement system of claim 12, wherein the camera and the plurality of fiber optic filaments are independently retractable through the tube.

15. The temporary tube placement system of claim 12, wherein the working lumen of the tube increases in cross section from the proximal end portion toward the distal end portion along at least a portion of the tube.

16. The temporary tube placement system of claim 6, wherein the camera and the plurality of fiber optic filaments are independently retractable through the tube.

17. The temporary tube placement system of claim 16, wherein the working lumen of the tube increases in cross section from the proximal end portion toward the distal end portion along at least a portion of the tube.

18. The temporary tube placement system of claim 6, wherein the working lumen of the tube increases in cross section from the proximal end portion toward the distal end portion along at least a portion of the tube.

19. The temporary tube placement system of claim 6, further comprising a screen for displaying images from the camera; and a power source electrically attached to the camera and the light source.

\* \* \* \* \*